(12) United States Patent
Hoecke et al.

(10) Patent No.: US 7,753,696 B2
(45) Date of Patent: Jul. 13, 2010

(54) LEAD TERMINAL MULTI-TOOL

(75) Inventors: Kyle Hoecke, Lino Lakes, MN (US); Gregory L. Sundberg, Stillwater, MN (US); Michelle Fangmeier, Blaine, MN (US); Bryan D. Johnson, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 25 days.

(21) Appl. No.: 11/127,886

(22) Filed: May 12, 2005

(65) Prior Publication Data

US 2006/0258193 A1 Nov. 16, 2006

(51) Int. Cl.
*H01R 4/66* (2006.01)
(52) U.S. Cl. ...................................................... 439/92
(58) Field of Classification Search ................ 439/92, 439/160, 169, 909; 600/373, 374, 585; 607/36, 607/115, 122; 606/41
See application file for complete search history.

(56) References Cited

U.S. PATENT DOCUMENTS

| | | | |
|---|---|---|---|
| 3,221,291 A | 11/1965 | Pratt | |
| 4,002,399 A | 1/1977 | Deitch et al. | |
| 4,165,147 A | 8/1979 | Buck | |
| 4,178,052 A | 12/1979 | Ekbom et al. | |
| 4,209,019 A | 6/1980 | Dutcher et al. | |
| 4,214,132 A | 7/1980 | Kelso | |
| 4,221,451 A | 9/1980 | Petrelewicz | |
| 4,245,642 A | 1/1981 | Skubitz et al. | |
| 4,347,842 A | 9/1982 | Beale | |
| 4,364,625 A | 12/1982 | Baker et al. | |
| 4,620,765 A | 11/1986 | Knickerbocker | |
| 4,624,266 A | 11/1986 | Kane | |
| 4,655,535 A | 4/1987 | Kysiak | |

(Continued)

FOREIGN PATENT DOCUMENTS

EP 0005861 B1 12/1979

(Continued)

OTHER PUBLICATIONS

"Active Implantable Medical Devices—Four-pole Connector System for Implantable Cardiac Rhythm Management Devices", *ISO Draft International Standard*, (Nov. 21, 2003),64 pages.

(Continued)

*Primary Examiner*—Mark W Bockelman
*Assistant Examiner*—Roland Dinga
(74) *Attorney, Agent, or Firm*—Faegre & Benson LLP

(57) ABSTRACT

The document discusses, among other things, apparatuses, assemblies, and methods for facilitating the installation of an implantable lead into a subject. In one example, the apparatus includes a housing having a lead terminal passageway on a first end and having an introductory opening on a second end. The lead terminal passageway is adapted to be inserted over a lead terminal end. The introductory opening is adapted to accept a stylet and guide it into a pin lumen. In another example, the apparatus includes one or both of at least one protective terminal contact device and a securing contact device allowing electrical contact to be made with a lead terminal ring or a lead terminal pin without damaging or bridging between such elements of the lead terminal end. The securing contact device is also adapted to mechanically engage the lead terminal pin thereto for facilitating actuation of fixation devices.

19 Claims, 9 Drawing Sheets

U.S. PATENT DOCUMENTS

| | | | |
|---|---|---|---|
| 4,695,116 | A | 9/1987 | Bailey et al. |
| 4,705,485 | A | 11/1987 | Hansen |
| 4,744,370 | A | 5/1988 | Harris |
| 4,846,719 | A | 7/1989 | Iwashita |
| 4,858,810 | A | 8/1989 | Intlekofer et al. |
| 4,867,708 | A | 9/1989 | Iizuka |
| 5,211,637 | A | 5/1993 | Goto et al. |
| 5,336,246 | A * | 8/1994 | Dantanarayana ............. 607/37 |
| 5,354,326 | A | 10/1994 | Comben et al. |
| 5,454,739 | A | 10/1995 | Strand |
| 5,477,856 | A * | 12/1995 | Lundquist ................... 600/373 |
| 5,531,699 | A | 7/1996 | Tomba et al. |
| 5,535,745 | A | 7/1996 | Ingram et al. |
| 5,558,547 | A | 9/1996 | Breitschaft et al. |
| 5,645,440 | A | 7/1997 | Tobler et al. |
| 5,679,022 | A | 10/1997 | Cappa et al. |
| 5,687,213 | A | 11/1997 | Larkin |
| 5,713,925 | A | 2/1998 | Sullivan et al. |
| 5,752,915 | A | 5/1998 | Neubauer et al. |
| 5,800,375 | A * | 9/1998 | Sweezer et al. ............ 604/4.01 |
| 5,919,213 | A | 7/1999 | Nelson et al. |
| 5,934,925 | A | 8/1999 | Tobler et al. |
| 5,944,562 | A | 8/1999 | Christensson |
| 5,987,344 | A * | 11/1999 | West ........................... 600/373 |
| 6,038,481 | A | 3/2000 | Werner et al. |
| 6,062,902 | A | 5/2000 | Buckles et al. |
| 6,116,959 | A | 9/2000 | Taylor |
| 6,132,390 | A | 10/2000 | Cookston et al. |
| 6,149,448 | A | 11/2000 | Haller et al. |
| 6,162,101 | A | 12/2000 | Fischer et al. |
| 6,203,506 | B1 | 3/2001 | Bostrom |
| 6,206,870 | B1 | 3/2001 | Kanner |
| 6,212,434 | B1 * | 4/2001 | Scheiner et al. ............. 607/123 |
| 6,244,905 | B1 | 6/2001 | Wang |
| 6,263,224 | B1 * | 7/2001 | West ........................... 600/373 |
| 6,280,213 | B1 | 8/2001 | Tobler et al. |
| 6,343,233 | B1 | 1/2002 | Werner et al. |
| D457,494 | S | 5/2002 | Lin |
| 6,397,108 | B1 | 5/2002 | Camps et al. |
| 6,400,976 | B1 | 6/2002 | Champeau |
| 6,415,168 | B1 | 7/2002 | Putz |
| 6,463,334 | B1 * | 10/2002 | Flynn et al. ................. 607/127 |
| 6,478,594 | B1 | 11/2002 | Curtin et al. |
| 6,501,990 | B1 * | 12/2002 | Sundberg et al. ............ 607/122 |
| 6,580,948 | B2 | 6/2003 | Haupert et al. |
| 6,602,242 | B1 * | 8/2003 | Fung et al. .................. 604/528 |
| 6,697,676 | B2 * | 2/2004 | Dahl et al. .................. 607/126 |
| 6,733,500 | B2 * | 5/2004 | Kelley et al. ................. 606/41 |
| 6,743,031 | B2 | 6/2004 | Baumgaertner et al. |
| 6,746,412 | B1 | 6/2004 | Hill et al. |
| 6,758,854 | B1 * | 7/2004 | Butler et al. ................. 606/194 |
| 6,799,991 | B2 | 10/2004 | Williams et al. |
| 6,836,687 | B2 * | 12/2004 | Kelley et al. ................ 607/122 |
| 6,901,288 | B2 * | 5/2005 | Janke et al. .................... 607/9 |
| 6,915,169 | B2 * | 7/2005 | Flynn et al. ................. 607/122 |
| 6,931,286 | B2 * | 8/2005 | Sigg et al. ................... 607/120 |
| 6,970,747 | B2 | 11/2005 | Kokones et al. |
| 6,983,185 | B2 * | 1/2006 | Ley et al. .................... 607/122 |
| 7,130,699 | B2 * | 10/2006 | Huff et al. ................... 607/116 |
| 7,158,838 | B2 * | 1/2007 | Seifert et al. ................ 607/127 |
| 7,174,219 | B2 * | 2/2007 | Wahlstrand et al. ......... 607/116 |
| 7,187,971 | B2 * | 3/2007 | Sommer et al. ................ 607/3 |
| 2002/0007198 | A1 | 1/2002 | Haupert et al. |
| 2003/0163184 | A1 * | 8/2003 | Scheiner et al. ............. 607/122 |
| 2003/0199948 | A1 | 10/2003 | Kokones et al. |
| 2004/0092946 | A1 * | 5/2004 | Bagga et al. .................. 606/93 |
| 2004/0116878 | A1 * | 6/2004 | Byrd et al. ................... 604/263 |
| 2004/0147963 | A1 * | 7/2004 | Sommer et al. ................ 607/3 |
| 2004/0215302 | A1 | 10/2004 | Sage et al. |
| 2004/0230268 | A1 * | 11/2004 | Huff et al. ................... 607/116 |
| 2005/0015048 | A1 * | 1/2005 | Chiu et al. ............. 604/101.04 |
| 2005/0085885 | A1 * | 4/2005 | Janke et al. .................. 607/122 |
| 2005/0177199 | A1 | 8/2005 | Hansen et al. |
| 2005/0267557 | A1 * | 12/2005 | Flynn et al. ................. 607/127 |
| 2006/0089698 | A1 * | 4/2006 | Sundberg et al. ............ 607/122 |

FOREIGN PATENT DOCUMENTS

| | | |
|---|---|---|
| EP | 0587379 A2 | 3/1994 |
| GB | 974786 | 11/1964 |
| JP | 2001068377 A * | 3/2001 |
| WO | WO-0056402 A1 | 9/2000 |
| WO | WO-2005077453 A2 | 8/2005 |
| WO | WO-2005077453 A3 | 8/2005 |

OTHER PUBLICATIONS

"ISO International Standard 5841-3: 2000 Technical Corrigendum 1", (Nov. 15, 2003),2 pages.

"Physician's Manual—Easytrak 2: Coronary Venous Steroid-Eluting Dual-Electrode Pace/Sense Lead", Available at: http://www.guidant.com/products/TemplatePDFs/355898_002.pdf, Guidant Physician Manual for Easytrak 2 Leads.,29.

ISO, "Implants for Surgery-Cardiac Pacemakers—Part 3: Low-profile connectors [IS-1] for implantable pacemakers", *International Standard Organization, ISO 5841-3: (2000) Second Edition*, (Oct. 15, 2000),18 pgs.

"U.S. Appl. No. 10/776,661, Prosecution File History", 55 pgs.

"PCT Application No. PCT/US2005/002888, International Preliminary Report on Patentability mailed Aug. 24, 2006", 9 pgs.

"U.S. Appl. No. 10/776,661, Non-Final Action mailed Dec. 20, 2007", 5 pgs.

"XEL & XJL Insulation Piercing Lead Sets", (undated), 1 pg.

"U.S. Appl. No. 10/776,661 Final Office Action mailed Jul. 1, 2008", 7 pgs.

"U.S. Appl. No. 10/776,661, Final Office Action mailed Jan. 22, 2009", 5 pgs.

"DBS™ Lead Kit for Deep Brain Stimulation", © Medtronic, Inc. 2002, (2002), 14 pgs.

"PCT Application No. PCT/US2005/002888, International Search Report mailed Sep. 2, 2005", 6 pgs.

Lauro, B. R., et al., "A Low Cost, Disposable, Zero Insertion Force Cable Connector for Trial Spinal Cord Stimulation", *Proceedings of The First Joint BMES/EMBS Conference Serving Humanity. Advancing Technology*, (Oct. 13-16, 1999, Atlanta, GA), (1999), p. 594.

* cited by examiner

LEAD TERMINAL MULTI-TOOL

TECHNICAL FIELD

This document pertains generally to an implantable lead, and more particularly, but not by way of limitation, to apparatuses, assemblies, and methods for installation of an implantable lead into a subject.

BACKGROUND

Leads represent the electrical link between an implantable medical device (IMD) and a subject's cardiac tissue, which is to be excited or stored. A lead may include a single or multiple conductors that are connected to an electrode or an electrode assembly at a lead intermediate portion or lead distal end. A connector is included at a lead terminal end to form an electrical connection between the electrode or electrode assembly and the IMD. The connector typically includes lead terminal contacts, such as a lead terminal pin or at least one lead terminal ring.

To implant the lead with the subject, the lead is often fed intravenously toward the subject's heart. To facilitate the difficult travel of the lead through the subject, lead and their corresponding elements, such as the lead terminal contacts, are being designed smaller. This smaller size makes access to lead elements inherently more difficult for an implanting physician. Also influencing a reduction in the size of the lead elements, specifically the lead terminal contacts, is the advent of multipolar inline lead terminal technology.

Once the lead is implanted within the subject and the electrode or electrode assembly is positioned at a desired location within, on, or about the subject's heart, it is often desirable to provide some method for securing the electrode or electrode assembly at that precise location. Mechanical fixation devices may be used to firmly anchor the electrode or electrode assembly at the desired location. One type of mechanical fixation device used is a fixation helix, which anchors the lead distal end. The fixation helix is typically extended and screwed into cardiac tissue by applying a torque to the other end of the conductor that the fixation helix is engaged with or by rotating the lead itself.

After anchoring the lead distal end, the implanting physician will often establish an electrical connection between at least one electrode and a test or stimulation system, such as a pacing system analyzer (PSA). To make this electrical connection, a clip(s) (e.g., an alligator clip) coupled to one end of an analyzer conductor(s) (e.g., cable) is typically attached directly to the lead terminal pin and the at least one lead terminal ring. This direct contact between the clip(s) and the lead may permanently damage the lead at the point(s) of attachment. For instance, the attachment or subsequent detachment of the clip may severely scratch (e.g., groove) the lead. Additionally, the tighter axial spacing of the electrical contacts (e.g. lead terminal rings or lead terminal pin), which is a byproduct of multipolar inline lead terminal technology, may result in the clip attachment bridging between two or more electrical contacts thereby impeding testing or stimulation.

Accordingly, what is needed is an apparatus which prevents damage to a lead and facilitates installation of the lead in many ways, thereby saving the implanting physician valuable time and effort.

SUMMARY

An apparatus includes a housing extending from a housing first end to a housing second end. The housing first end includes a lead terminal passageway, while the housing second end includes an introductory opening. The lead terminal passageway has a diameter greater than an outer diameter of a lead terminal end, allowing the housing to be inserted over (at least a portion of) the lead terminal end. The introductory opening includes a first diameter, which narrows to a diameter greater than an outer diameter of a stylet. The lead terminal passageway and the introductory opening communicatively couple within the housing. Also incorporated with the housing is at least one protective terminal contact device. Each protective terminal contact device includes an exterior and interior electrically conductive portion. In varying examples, the electrically conductive portions allow for electrical engagement between an analyzer conductor and a lead terminal pin and at least one lead terminal ring.

Several options for the apparatus are as follows. In one example, the apparatus further includes a securing contact device incorporated with the housing. In one such example, the securing contact device may engage a lead terminal pin when the pin is located within the housing. In another example, the housing includes at least one notch. In one such example, the at least one notch allows an electrical connection to be made directly with the lead terminal pin by the analyzer conductor. In yet another example, the housing includes two sections, a housing first section and a housing second section, the housing second section being rotatable independent from the housing first section. Other options are as follows. In one example, one or both of the at least one protective terminal contact device and the securing contact device include a terminal contact indicator to direct a user (e.g., implanting physician) as to where to attach the analyzer conductor(s). In another example, the apparatus includes a rotational handle. In a further example, one or both of the at least one protective terminal contact device and the securing contact device are radiopaque.

An assembly includes an apparatus, as described above, and a lead extending from a lead terminal end to a lead distal end. The lead terminal end includes a lead terminal pin and at least one lead terminal ring. In the assembly, the apparatus is adapted to be inserted over the lead terminal end. In one example, the assembly further includes a stylet adapted to be insertable through an introductory opening of the apparatus. In another example, the assembly further includes a rotational handle engageable with the apparatus to facilitate rotation of the lead terminal pin.

A method of using an apparatus, as described above, includes inserting an apparatus housing over a lead terminal pin and at least a portion of one or more lead terminal rings, advancing a stylet through a second end of the apparatus housing and subsequently into the lead, and electrically engaging an analyzer conductor with a combination of the lead terminal pin and the at least one lead terminal ring. Several options for this method are possible. In one example, the method further includes extending or retracting an active fixation mechanism located at a lead distal end. In another example, the method further includes detecting or delivering an electrical signal to/from a subject using one or both of the lead terminal pin and the at least one lead terminal ring.

A method of making an apparatus, as described above, includes forming an apparatus housing insertable over a lead terminal end on an apparatus housing first end and having an introductory opening on an apparatus housing second end, incorporating a protective terminal contact device with the apparatus housing, and incorporating a securing contact device with the apparatus housing. Several options for this method are possible. In one example, forming the apparatus housing includes forming a housing first section and a housing second section. In another example, the method further includes forming a rotational handle engageable with the apparatus housing. In yet another example, the method further includes incorporating at least one terminal contact indicator with one or both of the at least one protective terminal contact device and the securing contact device.

Advantageously, the size, shape and structure of the present apparatus allows numerous lead installation steps to be met by a single embodiment. By so doing, the apparatus reduces or eliminates the cumbersome array of tools currently required in lead installation. As an example, the apparatus provides, in varying examples, an introductory opening (e.g., stylet guide) on a housing second end which facilitates the insertion of a stylet into a lead. As another example, the apparatus overcomes the problem associated with small lead elements (e.g., lead terminal contacts) by bringing access to such elements to a more implanter-friendly location and protecting such lead elements from attachment/detachment damage. As a further example, the apparatus provides retention or handle features for driving the lead terminal pin on active fixation leads. Moreover, the apparatus is useful for various lead constructions. For instance, the apparatus is useful for unipolar, multipolar, uniradial, and co-radial lead constructions.

These and other examples, aspects, advantages, and features of the present apparatuses, assemblies, and methods will be set forth in part in the detailed description, which follows, and in part will become apparent to those skilled in the art by reference to the following description of the present apparatuses, assemblies, and methods and referenced drawings or by practice of the same.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

The following detailed description includes references to the accompanying drawings, which form a part of this detailed description. The drawings show, by way of illustration, specific embodiments in which the present apparatuses, assemblies, and methods may be practiced. These embodiments, which are also referred to herein as "examples," are described in enough detail to enable those skilled in the art to practice the present apparatuses, assemblies, and methods. The embodiments may be combined, other embodiments may be utilized, or structural or logical changes may be made without departing from the scope of the present apparatuses, assemblies, and methods. It is also to be understood that the various embodiments of the present apparatuses, assemblies, and methods, although different, are not necessarily mutually exclusive. For example, a particular feature, structure or characteristic described in one embodiment may be included with other embodiments. The following detailed description is, therefore, not to be taken in a limiting sense, and the scope of the present invention is defined by the appended claims and their legal equivalents.

In this document: the terms "a" or "an" are used, as is common in patent documents, to include one or more than one; the term "or" is used to refer to a nonexclusive or, unless otherwise indicated; the term "stylet" is used to include guidewires or other similar structures for maintaining rigidity of the lead during lead implantation; the term "subject" is used to include the term "patient"; the term "contact device" is used to include, but is not limited to, thumbscrews, springs, switches, and the like; the term "opening" is used to include "cavity," "hole," "aperture," etc.; and the term "implantable medical device (IMD)" is used to include, but is not limited to, implantable cardiac rhythm management (CRM) systems such as pacemakers, cardioverter/defibrillators, pacer/ defibrillators, biventricular or other multi-site resynchronization or coordination devices such as cardiac resynchronization therapy (CRT) devices, and drug delivery systems.

Figure 1:
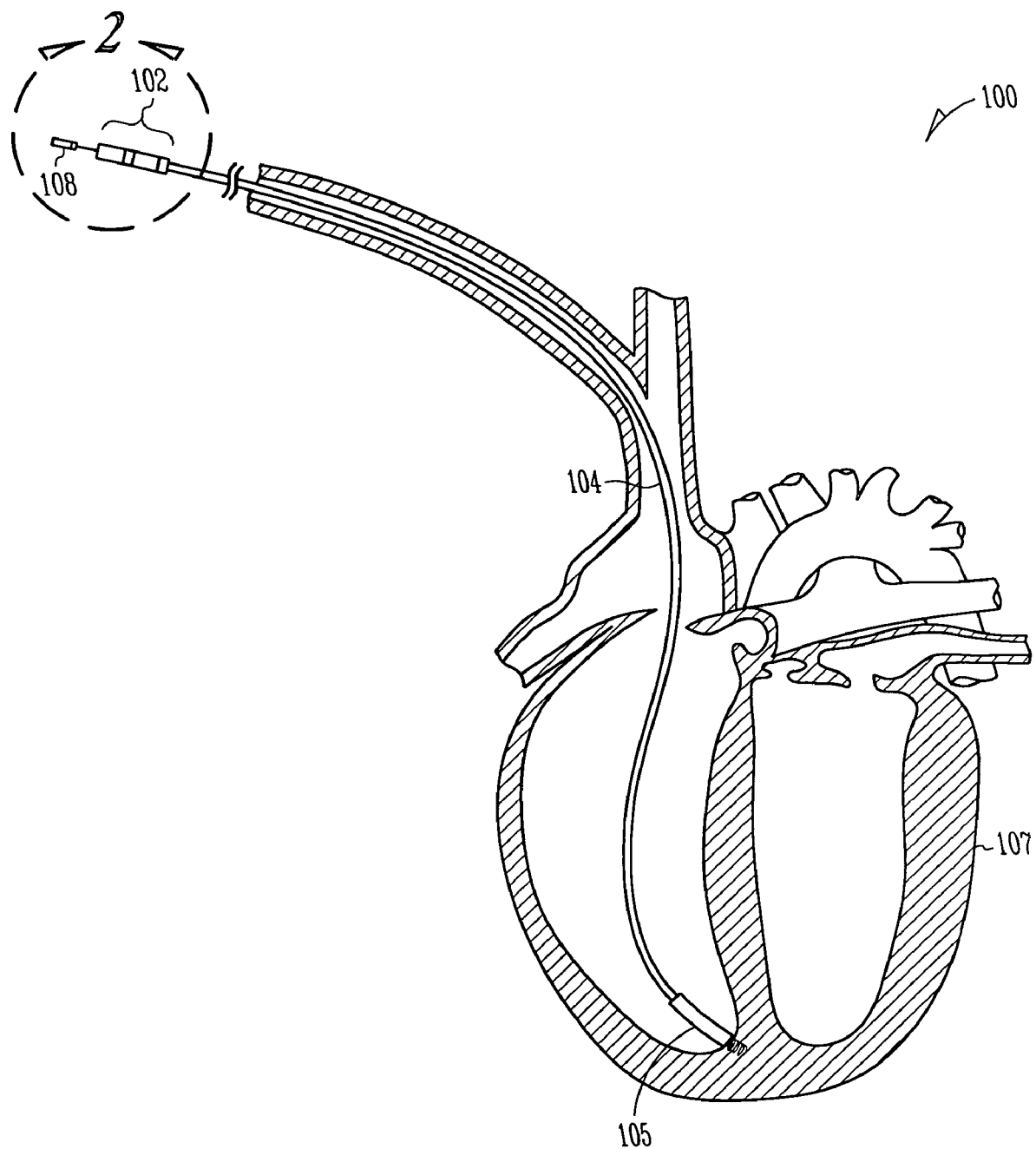
FIG. 1 is a perspective view illustrating an assembly and an environment in which the assembly may be used, as constructed in accordance with at least one embodiment.

FIG. 1 is a perspective view illustrating generally, an assembly 100 for use during an installation process of an implantable lead 104, and an environment in which assembly 100 is used. In one example, assembly 100 includes an apparatus 102, implantable lead 104, and a stylet 108. In another example, assembly 100 includes only apparatus 102 and implantable lead 104. A lead distal end 105 of implantable lead 104 may be located as desired by an implanting physician within, on, or about a heart 107 of a subject. In the illustrative example of FIG. 1, lead distal end 105 of implantable lead 104 is located in an apex of the right ventricle of heart 107.

Figure 2A:
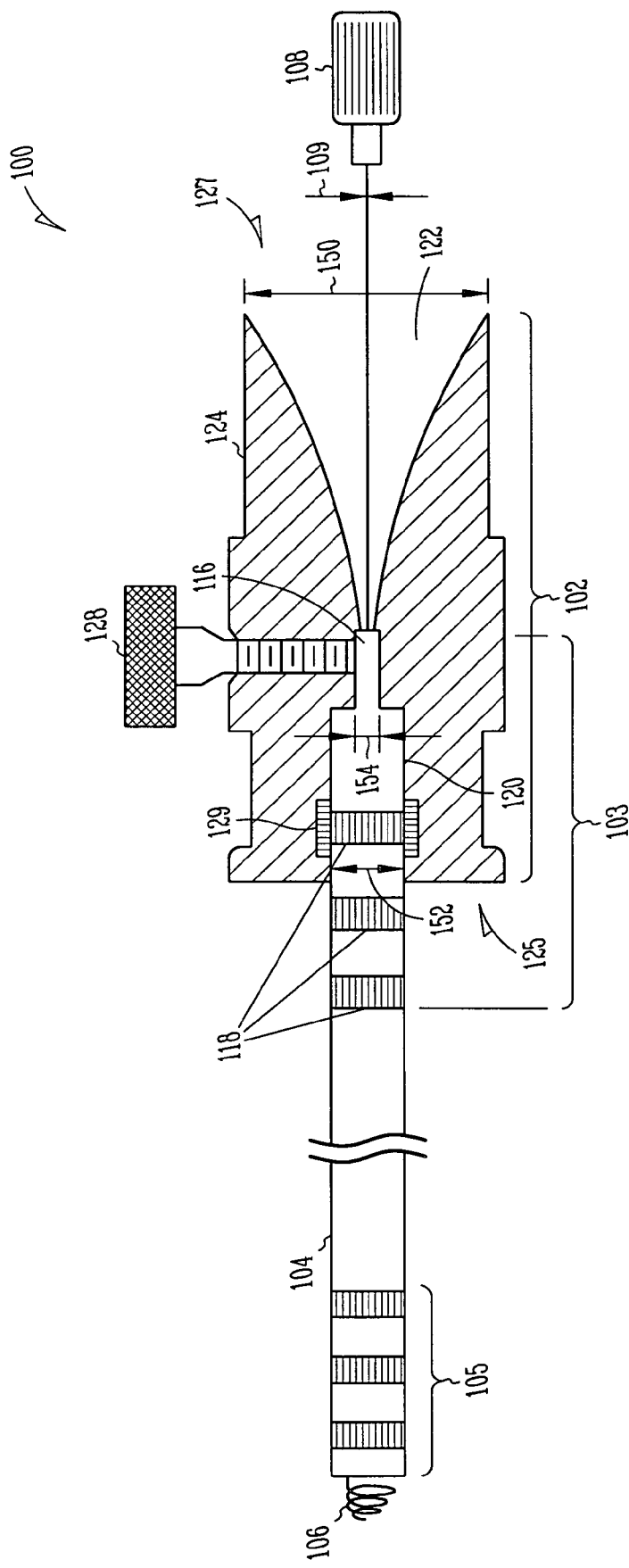
FIG. 2A is a detailed cross-sectional view illustrating the assembly of FIG. 1, as constructed in accordance with at least one embodiment.

FIG. 2A is a cross-sectional view illustrating in greater detail, by way of example, an assembly 100 including an apparatus 102, an implantable lead 104, and a stylet 108. In one example, apparatus 102 includes a housing 124 and a securing contact device 128. Housing 124 includes a lead terminal passageway 120 on a housing first end 125 and an introductory opening 122 on a housing second end 127. In another example, apparatus 102 includes at least one protective terminal contact device 129 (see also FIGS. 3A-3C, 4A-4B, and 5A). In yet another example, housing 124 includes a notch 140 (FIG. 5A). Notch 140 (FIG. 5A) allows an electrical connection to be made directly with a lead terminal pin 116 by an analyzer conductor 136 (FIGS. 4A-4B). In one example, analyzer conductor 136 (FIGS. 4A-4B) includes a cable having a clip (e.g., alligator clip) on a cable first end and connected to a test/stimulation system, such as a pacing system analyzer (PSA), on a cable second end. A PSA is a system typically used by an implanting physician for analyzing and verifying the performance of a system, such as a pacing system, which includes an IMD and an implantable lead. A PSA is configured to test the implantable lead for proper operation and for programming of the IMD, not only while connected in a simulated environment, but also while operating in an actual environment (e.g., when implanted in a subject). Moreover, a PSA is preferably equipped to generate pacing pulses as required to support the subject during the implantation process, independently of the IMD to be implanted.

In the example of FIG. 2A, lead terminal passageway 120 is sized and shaped to physically mate with a lead terminal end 103 of implantable lead 104. As a result, apparatus 102 may be inserted over at least a portion of lead terminal end 103. In another example, lead terminal pin 116 is thereafter or thereby engaged with housing 124 by securing contact device 128. Securing contact device 128 is adapted, in many examples, to electrically engage analyzer conductor 136 (FIGS. 4A-4B) with lead terminal pin 116.

In the example of FIG. 2A, an opening diameter 150 of introductory opening 122 is greater than a diameter 152 of a first end of lead terminal passageway 120; however, the present apparatus is not so limited. In another example, diameter 150 is less than or equal to diameter 152 of the first end of lead terminal passageway 120. In another example, introductory opening 122 continuously narrows to a diameter greater than an outer diameter 109 of stylet 108. In a further example, introductory opening 122 continuously narrows to a diameter substantially equal to or less than a diameter 154 of a second end of lead terminal passageway 120.

In many examples, lead terminal pin 116 of implantable lead 104 includes a pin lumen 131 (FIG. 6B) allowing stylet 108 to be advanced into implantable lead 104 during implantation. To this end, introductory opening 122 communicatively couples with lead terminal passageway 120 within housing 124, thereby allowing stylet 108 to be inserted into introductory opening 122 and pushed through lead terminal passageway 120 to pin lumen 131. In other examples, however, lead terminal pin 116 is solid and does not allow stylet 108 to pass though into implantable lead 104.

Figure 2B:
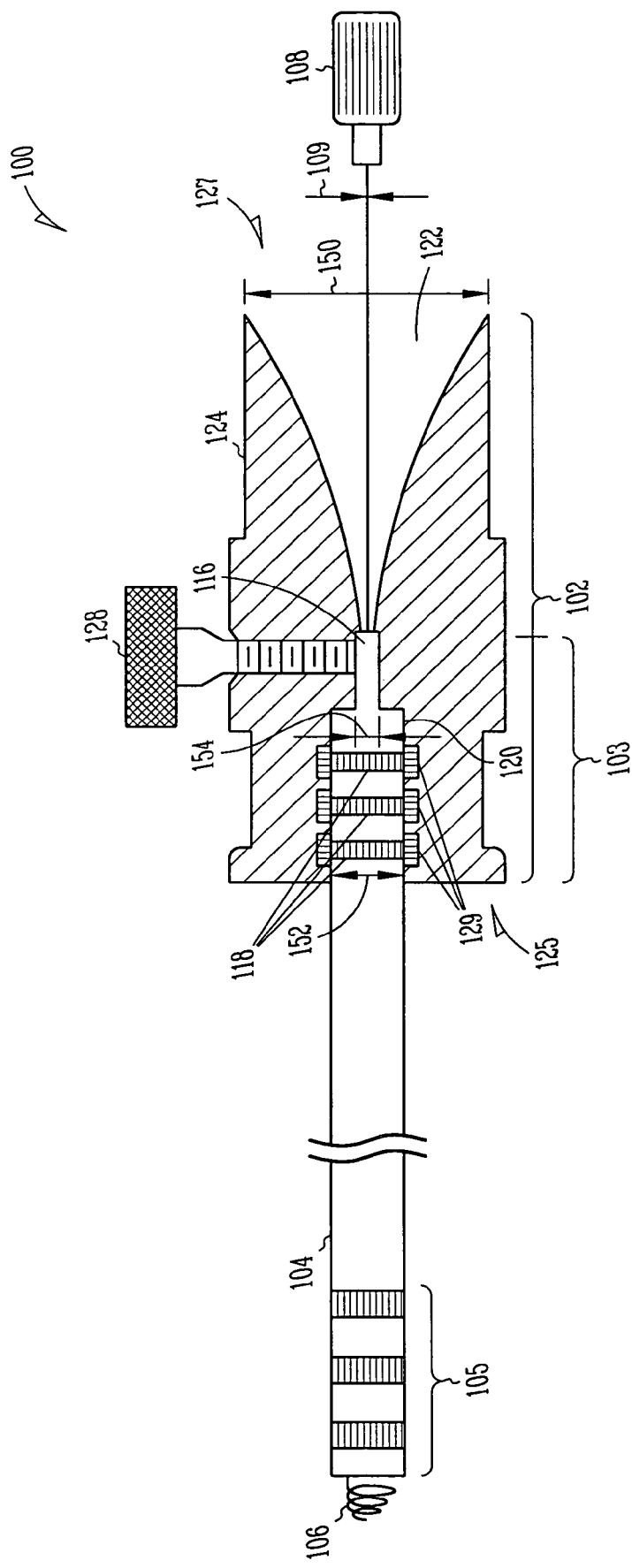
FIG. 2B is a detailed cross-sectional view illustrating the assembly of FIG. 1, as constructed in accordance with at least one embodiment.

As shown in the example of FIG. 2A, lead terminal passageway 120 may include a profile mating that of lead terminal end 103. As a result of such mating profiles, apparatus 102 may only be inserted over implantable lead 104 to a certain position on the lead 104. In one example, the mating profiles allow apparatus 102 to be inserted over lead terminal pin 116 and at least a portion of one or more lead terminal rings 118. In another example, as shown in FIG. 2B, the mating profiles allow apparatus 102 to be inserted over lead terminal pin 116 and all lead terminal rings 118. Advantageously, the mating profiles allow for easy alignment of implantable lead 104 with apparatus 102. For instance, the profiles may be positioned such that when apparatus 102 is fully inserted over implantable lead 104, protective terminal contact device(s) 129 aligns with at least one lead terminal ring(s) 118 (or portion thereof) and securing contact device 128 or notch 140 (FIG. 5A) aligns with lead terminal pin 116. Other means for generating alignment between implantable lead 104 and apparatus 102 include grooving or notching of the lead terminal end 103 or housing 124.

The implantable lead 104 includes, in varying examples, features to allow the lead 104 to be fixated within the subject. For example, in one option, implantable lead 104 includes passive fixation features, such as one or more tines. In another option, implantable lead 104 includes an active fixation assembly, such as a fixation helix 106, located at lead distal end 105. In many such examples, fixation helix 106 is engageable by way of lead terminal pin 116. In the example of FIG. 2A, securing contact device 128 mechanically engages lead terminal pin 116 with housing 124. Thus, when housing 124 is rotated, lead terminal pin 116 is caused to rotate. Lead terminal pin 116 may be rotated after lead distal end 105 of implantable lead 104 is positioned as desired by the implanting physician. In another example, fixation helix 106 is engageable by way of rotating implantable lead 104 itself.

Figure 3A:
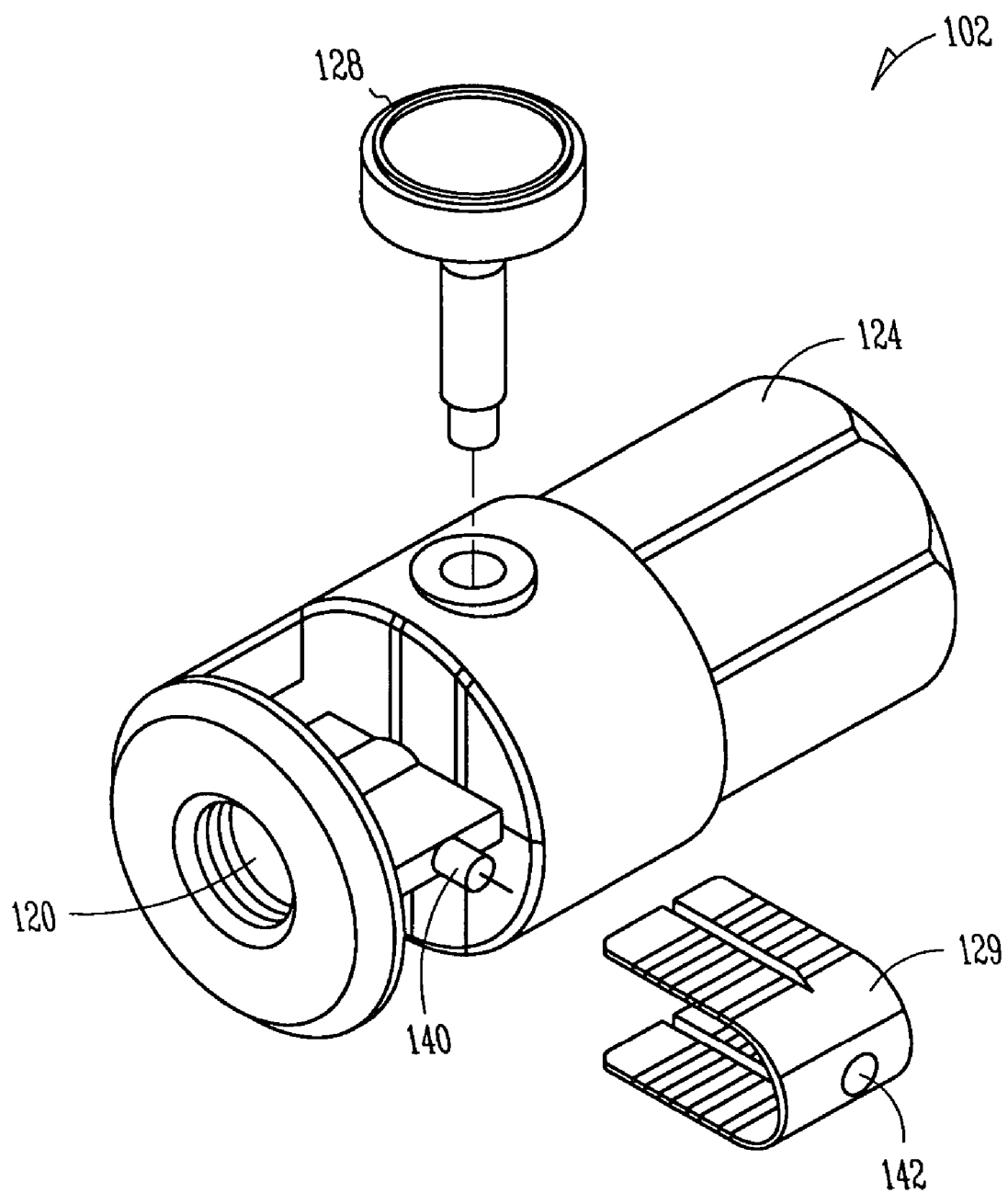
FIG. 3A is a perspective view illustrating elements of an apparatus, as constructed in accordance with at least one embodiment.
Figure 3B:
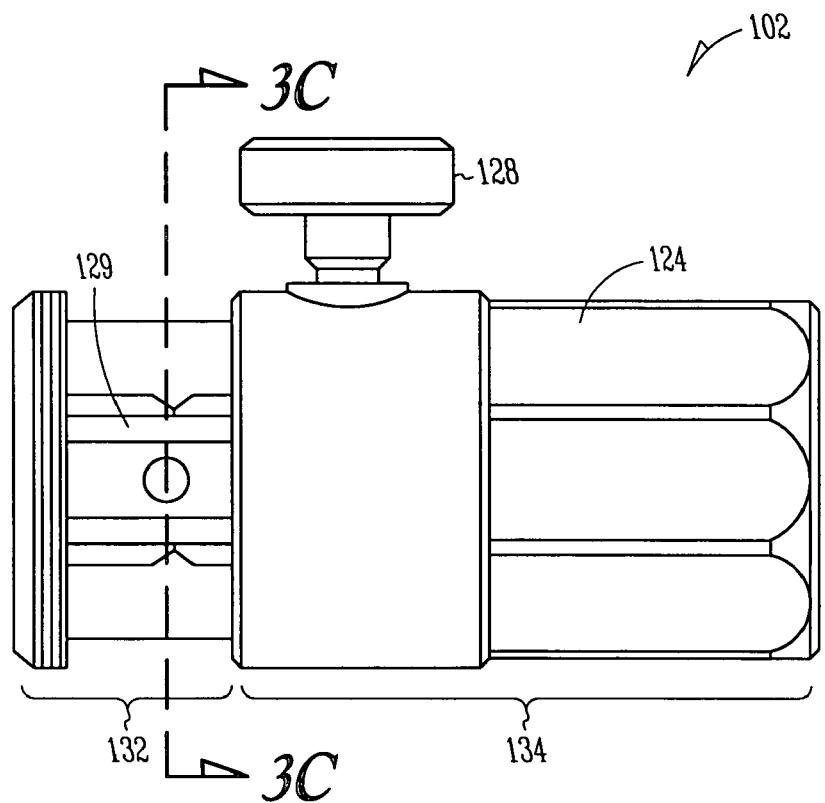
FIG. 3B is a side view of an apparatus, as constructed in accordance with at least one embodiment.
Figure 3C:
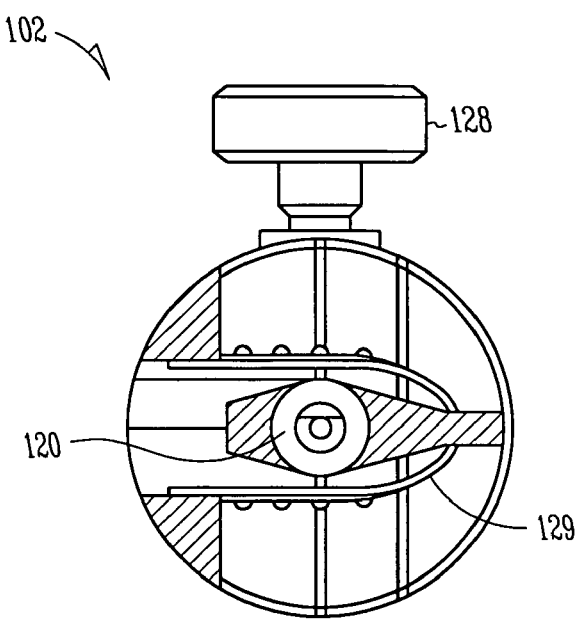
FIG. 3C is a cross-sectional view taken along 3C-3C of FIG. 3B.
Figure 4A:
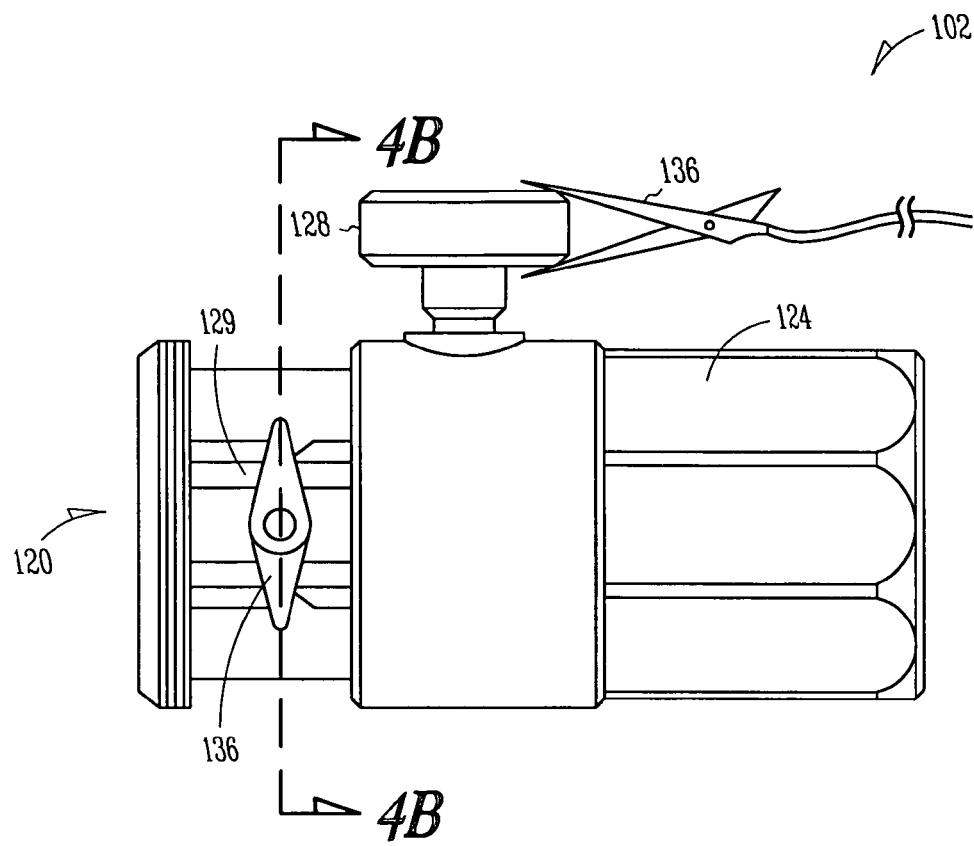
FIG. 4A is a side view of an apparatus connected to an analyzer conductor, as constructed in accordance with at least one embodiment.
Figure 4B:
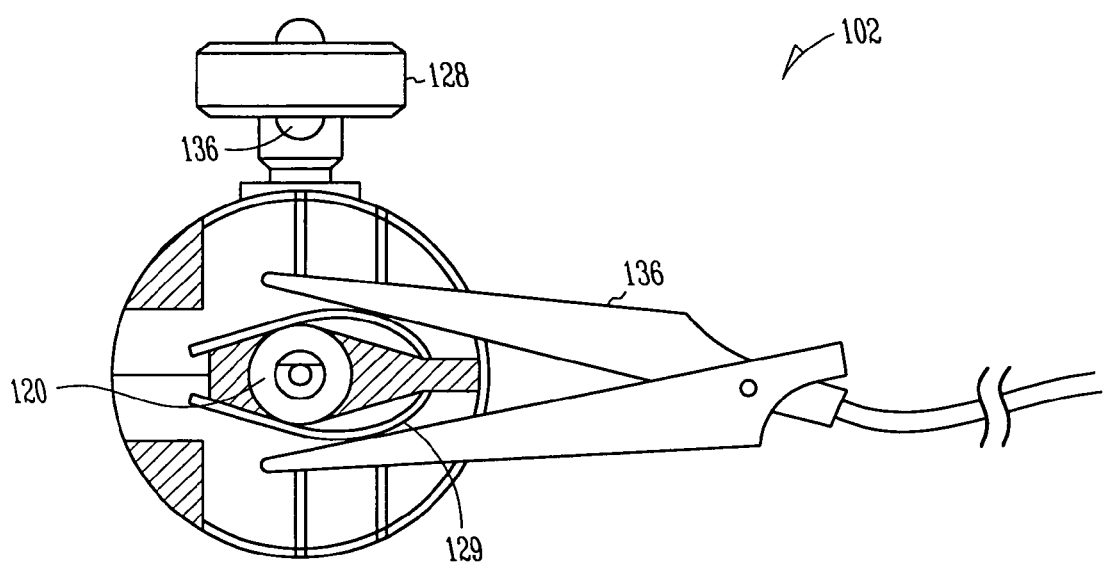
FIG. 4B is a cross-sectional view taken along 4B-4B of FIG. 4A.
Figures 5A, 5B:
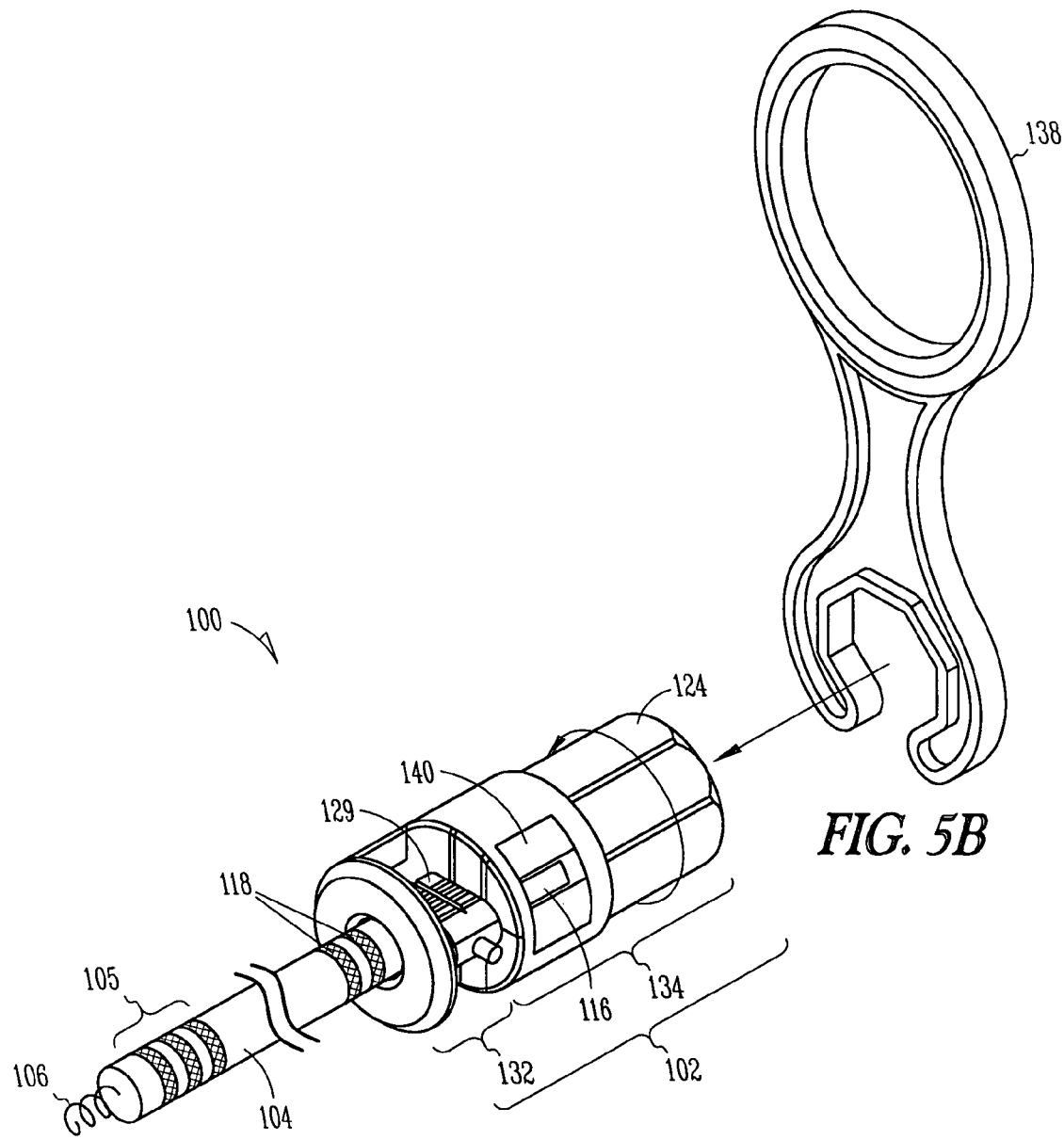
FIG. 5A is a perspective view illustrating an assembly, as constructed in accordance with at least one embodiment.
FIG. 5B is a perspective view illustrating an element of an assembly, as constructed in accordance with at least one embodiment.

FIGS. 3A-3C and 4A-4B illustrate in greater detail, by way of example, an apparatus 102 for use in the installation of an implantable lead 104 in a subject. FIG. 3A is an exploded perspective view illustrating elements of apparatus 102, such as a housing 124, a securing contact device 128, and a protective terminal contact device 129, which includes both interior and exterior electrically conductive portions. In one example, the electrically conductive portions are electrically conductive surfaces. In another example, apparatus 102 includes one protective terminal contact device 129. In another example, apparatus 102 includes a plurality of protective terminal contact devices 129. Protective terminal contact device 129 will be further discussed below, specifically in regards to the discussion of FIGS. 4A and 4B. Advantageously, in many examples, both protective terminal contact device 129 and securing contact device 128 are radiopaque, thereby allowing such elements to be opaque to various forms of radiation (e.g., X-rays).

As shown in FIG. 3A, protective terminal contact device 129 may include a stake hole 142, which is adapted to mate with a housing post 140. As a result, protective terminal contact device 129 may be coupled with housing 124, through the alignment and insertion of housing post 140 into stake hole 142. Thereafter, an exterior end of housing post 140 may be "heat staked" (e.g., melted), securing the protective terminal contact device 129 to housing 124. Although FIG. 3A illustrates the attachment of protective terminal contact device 129 to housing 124 via heat staking housing post 140 over stake hole 142, the present apparatus is not so limited. In other examples, protective terminal contact device 129 is coupled with housing 124 via over-molding, crimping, staking, press-fitting, snap-fitting, or interference-fitting securing means.

Referring to FIGS. 3A, 3B, and 3C, one example of the securing contact device 128 is illustrated. In these examples, securing contact device 128 is incorporated with housing 124. In varying examples, securing contact device 128 includes a first position and a second position, the first position allowing a lead terminal pin 116 (FIGS. 2, 6A) to be fully inserted into a lead terminal passageway 120, and the second position mechanically and electrically engaging lead terminal pin 116 (FIGS. 2, 6A) with securing contact device 128, and thus housing 124. In the example of FIG. 3C, one example of the second position of securing contact device 128 is shown. As illustrated, securing contact device 128 is a thumbscrew; however, the present apparatus is not so limited. In other examples, securing contact device includes a snap fit, a passive retention fit, or other similar securing means.

Figure 3D:
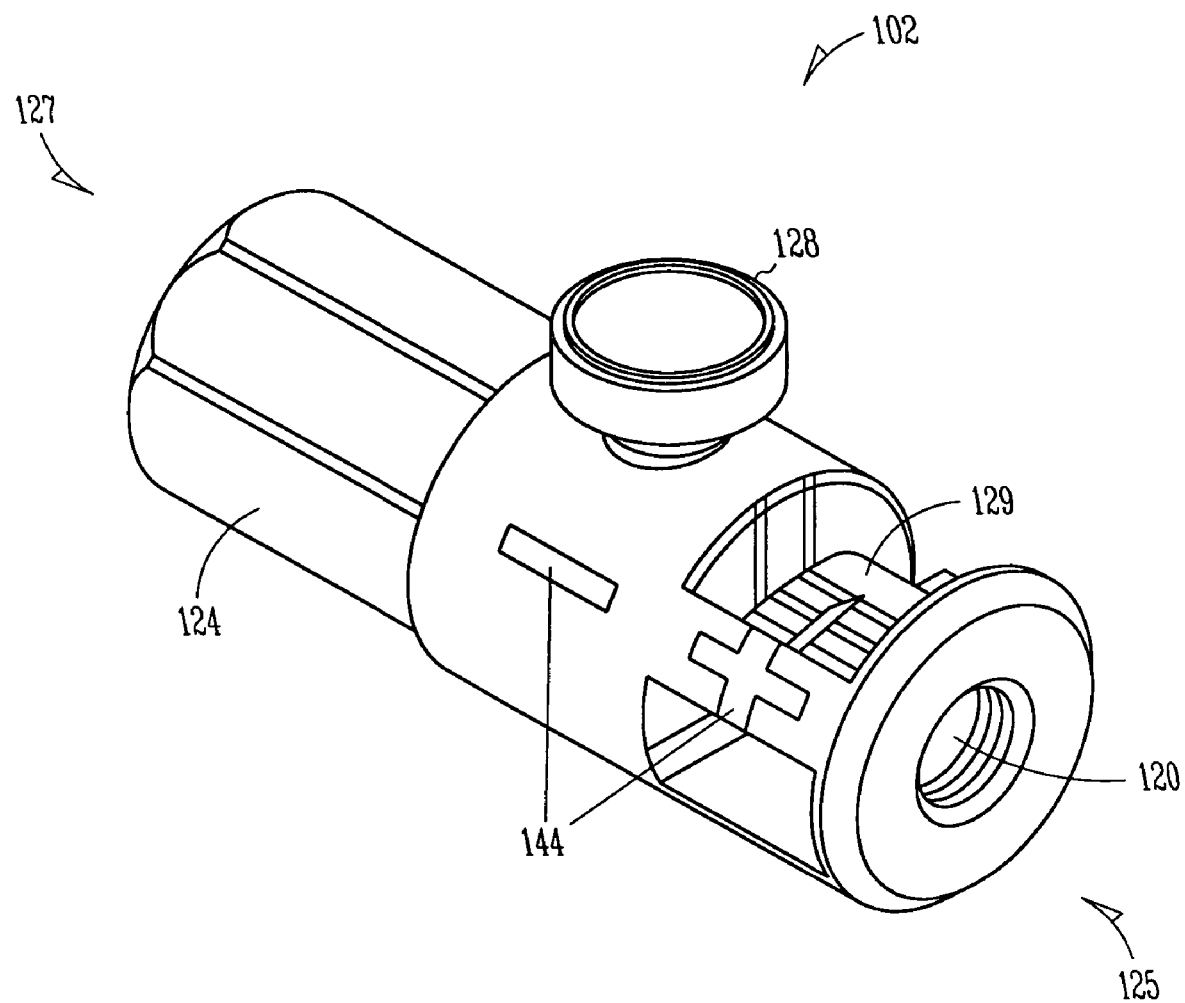
FIG. 3D is a perspective view illustrating elements of an apparatus, as constructed in accordance with at least one embodiment.

FIG. 3B is a side view illustrating generally, apparatus 102 as constructed in accordance with at least one embodiment. In this illustrative example, protective terminal contact device 129 and securing contact device 128 are engaged with housing 124. Both protective terminal contact device 129 and securing contact device 128 are elements of apparatus 102 which allow an electrical connection to be made between one or more analyzer conductor(s) 136 (FIGS. 4A-4B) and lead terminal pin 116 and at least one lead terminal ring 118 (FIG. 2A). Notably, to obtain a PSA reading, both a positive (+) and a negative (−) polarity connection must be established between the test/stimulation system and the electrical contacts of lead terminal end 103. Advantageously, protective terminal contact device 129 and securing contact device 128 allow an electrical connection to be made while at the same time protecting lead terminal end 103 (FIG. 2A) from potential damage resulting from each analyzer conductor's 136 (FIGS. 4A-4B) attachment or detachment from implantable lead 104 (FIG. 2A). In varying examples, protective terminal contact device 129 and securing contact device 128 provide a sufficiently accommodating portion for analyzer conductor 136 (FIGS. 4A-4B) to attach onto. In some examples, each protective terminal contact device 129 or securing contact device 128 includes a terminal contact indicator 144, as shown in FIG. 3D, to direct an implanting physician regarding as to which (alligator) clips (of analyzer conductor 136) attach to each electrical contact of implantable lead 104.

In one example, housing 124 includes two sections, a housing first section 132 and a housing second section 134. Typically, in such an example, housing second section 134 is rotatable independent from housing first section 132. As a result, when lead terminal pin 116 (FIGS. 2A-2B) is engaged with securing contact device 128, and thus housing second section 134, a fixation helix 106 (FIG. 2A) can be activated by rotating only housing second section 134 instead of having to rotate the entire housing 124 as is true in other examples. Thus, housing first section 132, which typically includes protective terminal contact device 129, does not have to rotate for engagement of fixation helix 106.

FIG. 3C is a cross-sectional view taken along line 3C-3C of FIG. 3B and illustrates a cross-section of apparatus 102, as constructed in accordance with at least one embodiment. As discussed above, lead terminal passageway 120 is insertable over lead terminal end 103 (FIG. 2A) of implantable lead 104 (FIG. 2A), such that alignment of securing contact device 128 and protective terminal contact device(s) 129 with lead terminal pin 116 (FIG. 2A) and at least a portion of one or more lead terminal ring(s) 118 (FIG. 2A), respectively, results.

FIG. 4A is a side view illustrating generally, one or more analyzer conductors 136 attached to an apparatus 102. Apparatus 102, in varying examples, includes a securing contact device 128 or a protective terminal contact device 129. In some examples, apparatus 102 includes a plurality of securing contact devices 128 or protective terminal contact devices 130. In the example of FIG. 4A, apparatus 102 includes both securing contact device 128 and protective terminal contact device 129 to which one or more analyzer conductors 136 are attached.

Advantageously, securing contact device 128 and protective terminal contact device 129 allow an electrical connection to be established between a lead terminal pin 116 (FIG. 2A) and a portion of one or more lead terminal ring(s) 118 (FIG. 2A) and a test/stimulation system, such as a PSA system, when a lead terminal end 103 (FIG. 2A) is inserted into a lead terminal passageway 120 of apparatus housing 124. For instance, when lead terminal end 103 (FIG. 2A) is inserted into lead terminal passageway 120 and lead terminal pin 116 (FIG. 2A) is secured to housing 124 by securing contact device 128, an electrical connection can be made between analyzer conductor 136 and lead terminal pin 116 (FIG. 2A). In this way, analyzer conductor is not attached directly to lead terminal end 103 (FIG. 2A), thereby preventing possible damage to end 103. Similarly, when lead terminal end 103 (FIG. 2A) is inserted into lead terminal passageway 120 and protective terminal contact device 129 aligns with a portion of one or more lead terminal rings 118 (FIG. 2A), an electrical connection can be made between analyzer conductor 136 and lead terminal ring 118 (FIG. 2A), thereby preventing possible damage to lead terminal end 103 (FIG. 2A).

FIG. 4B is a cross-sectional view taken along line 4B-4B of FIG. 4A illustrating generally, apparatus 102 as constructed in accordance with at least one embodiment. In the example of FIG. 4B, analyzer conductor 136 is attached to protective terminal contact device 129. In one example, when analyzer conductor 136 is engaged with protective terminal contact device 129, one or more legs of protective terminal contact device 129 are forced inward, towards one another, as illustrated in FIG. 4B. As a result, when lead terminal end 103 (FIG. 2A) of implantable lead 104 (FIG. 2A) is inserted into lead terminal passageway 120 (FIG. 2A), an electrical connection is established between analyzer conductor 136 and lead terminal pin 116 (FIG. 2A) and at least one lead terminal ring 118 (FIG. 2A).

As discussed above in regards to FIG. 4A, using protective terminal contact device 129 or securing contact device 128 to make an electrical connection between a conductive surface of implantable lead 104 (FIG. 2) and analyzer conductor 136, protects implantable lead 104 from possible attachment or detachment damage. Further, protective terminal contact device 129 and securing contact device 128 provide implanter-friendly conductive surfaces to which analyzer conductors 136 may be attached. Such attachment-conducive surfaces provide the advantage of dealing with the advent of multipolar inline lead terminal technology. Typically associated with multipolar inline lead terminal technology is tighter axial spacing of the electrical contacts (e.g., lead terminal rings 118 or lead terminal pin 116) on lead terminal end 103. Such tighter axial spacing results in smaller, more closely spaced electrical contacts to which an implanting physician must attempt to clamp onto with existing analyzer conductor(s) 136, which likely results in unintended misses or shorts (by the implanting physician) during testing/stimulation.

FIG. 5A is a perspective view illustrating generally, an assembly 100 including an implantable lead 104 and an apparatus 102. Apparatus 102 includes a housing 124 and a protection terminal contact device 129. In this example, housing 124 includes a housing first section 132 and a housing second section 134, in which housing second section 134 is rotatable independent from housing first section 132. As also shown in FIG. 5A, housing 124 further includes a notch 140. Notch 140 may permit access to a lead terminal pin 116 (FIG. 2A) by an analyzer conductor 136 (FIGS. 4A-4B). As a result, the implanting physician may take electrical measurements or provide electrical stimulation (e.g., make an electrical connection) with implantable lead's 104 electrical contacts without removal of apparatus 102.

FIG. 5B is a perspective view illustrating generally, an element of an assembly 100, specifically a rotational handle 138. In varying examples, rotational handle 138 may be engaged with housing 124 (FIG. 5A), which is typically engaged with the lead terminal pin 116. As mentioned above, implantable lead 104, in some examples, includes a fixation helix 106, which may be activated by rotation of lead terminal pin 116. In such an example, rotation of rotational handle 138 directly transmits rotational torque to housing 124 (FIG. 5A), which in turn transmits rotational torque to lead terminal pin 116, and thus fixation helix 106. The rotational torque thereby advances fixation helix 106 into a subject's cardiac tissue against which a lead distal end 105 was positioned when the rotation of fixation helix 106 began. In another example, rotational handle 138 is integrated with housing 124 (FIG. 5A).

Figure 6A:
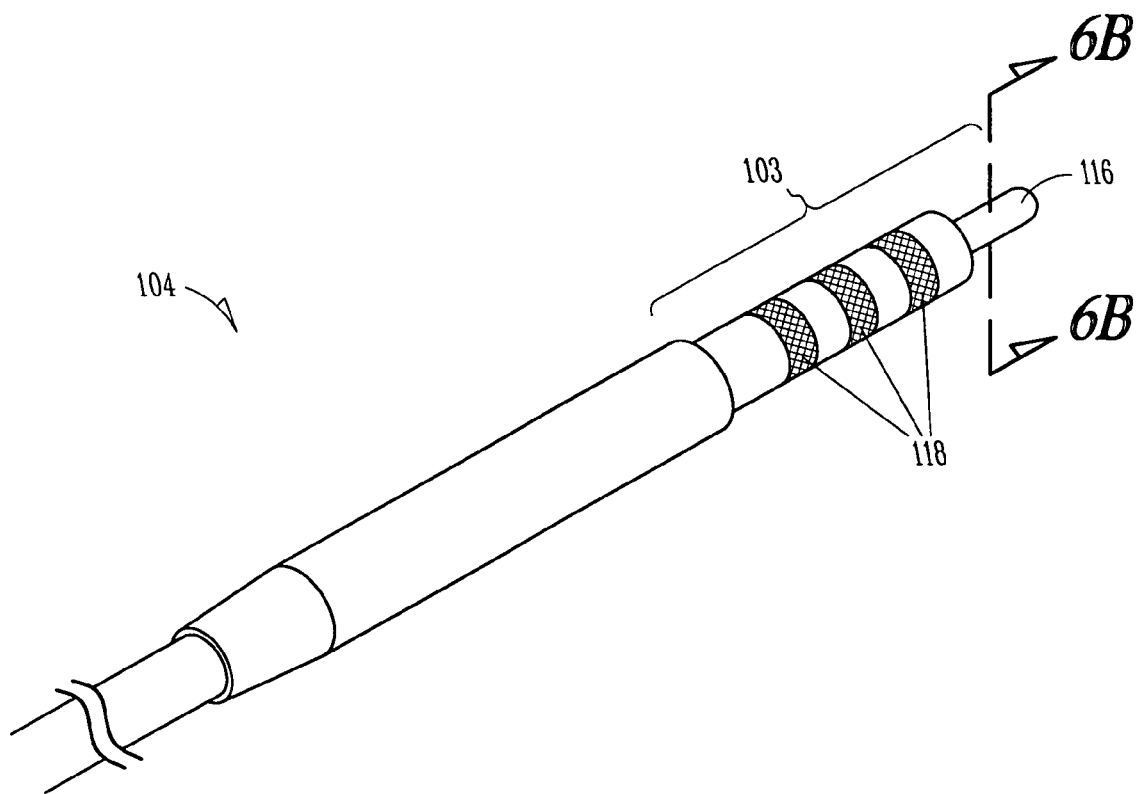
FIG. 6A is a perspective view illustrating an implantable lead, as constructed in accordance with at least one embodiment.
Figure 6B:
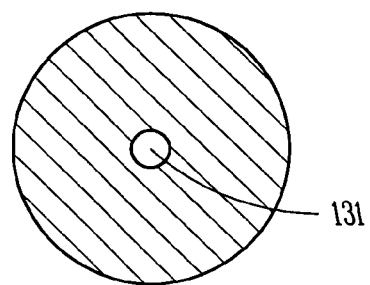
FIG. 6B is a cross-sectional view taken along 6B-6B of FIG. 6A.

FIGS. 6A-6B illustrate generally, a lead terminal end 103 of an implantable lead 104. FIG. 6A is a perspective view of one example of lead terminal end 103 of a multipolar inline lead. In varying examples, lead terminal end 103 includes a lead terminal pin 116 and at least one lead terminal ring 118. In this example, lead 104 includes three lead terminal rings 118.

FIG. 6B is a cross-sectional view of lead terminal pin 116 taken along line 6B-6B of FIG. 6A, as constructed in accordance with at least one embodiment. In one example, lead terminal pin 116 has a circular cross-sectional shape. In another example, lead terminal pin includes a pin lumen 131, which is typically sized and shaped to allow various stylets 108 (FIG. 2A) to pass therethrough. In a further example, as discussed above, lead terminal pin 116 may be solid.

A method of making an apparatus, including the apparatuses discussed above, includes forming an apparatus housing insertable over a lead terminal end on an apparatus housing first end and having an introductory opening on an apparatus housing second end, incorporating a protective terminal contact device with the apparatus housing, and incorporating a securing contact device with the apparatus housing.

Several options for this method are possible. In one example, forming the apparatus housing includes forming a housing first section and a housing second section. In another example, the method further includes forming a rotational handle engageable with the apparatus housing. In yet another example, the method further includes incorporating at least one terminal contact indicator with one or both of the at least one protective terminal contact device and the securing contact device. In a further example, the apparatus housing first end is sized and shaped to mate with the lead terminal end, such that the implantable lead is prohibited from advancing past a predetermined position when inserted into the apparatus.

A method of using an apparatus, including the apparatuses discussed above, includes inserting an apparatus housing over a lead terminal pin and at least a portion of one or more lead terminal rings, advancing a stylet through a second end of the apparatus housing and subsequently into an implantable lead, and electrically engaging analyzer conductors with a combination of the lead terminal pin and the at least one lead terminal ring. In one example, electrically engaging the analyzer conductor includes attaching the analyzer conductor to at least one protective terminal contact device incorporated with the apparatus housing. In another example, electrically engaging the analyzer conductor includes attaching the analyzer conductor to a securing contact device incorporated with the apparatus housing.

Several options for this method are possible. In one example, the method further includes extending or retracting an active fixation mechanism, such as a fixation helix, located at a lead distal end. In another example, the method further includes detecting or delivering an electrical signal to/from a subject using one or both of the lead terminal pin and the at least one lead terminal ring.

Advantageously, the present apparatuses, assemblies, and methods may provide an implanting physician with the ability to perform numerous functions using one embodiment. For instance, the present apparatus allows the physician to easily feed various stylets into a pin lumen of an implantable lead, make an electrical connection between one or more analyzer conductors and the lead terminal pin and one or more lead terminal rings, and engage a fixation helix. Furthermore, the apparatuses discussed above may be shipped already attached to an implantable lead forming one example of an assembly.

Although a multipolar lead design has been illustrated in the drawings, it should be understood that unipolar leads (that is a lead carrying one electrode and conductor) and multipolar leads of different configuration may readily utilize the novel structure of the present apparatus. It should also be understood that although the present apparatuses, assemblies, and methods have been described above, in large part, for use with a pacing and sensing lead for connecting a pacemaker to cardiac tissue, the same may be readily utilized with other types of leads.

As mentioned above, this Detailed Description is not to be taken in a limiting sense, and the scope of various embodiments is defined only by the appended claims, along with the full range of legal equivalents to which such claims are entitled.

What is claimed is:

1. An apparatus comprising:
   a housing, including a lead terminal passageway on a housing first end and an introductory opening on a housing second end, the lead terminal passageway and the introductory opening communicatively coupling within the housing;
   at least one protective terminal contact device incorporated with the housing, each protective terminal contact device including an exterior electrically conductive portion accessible from outside the housing while a stylet is disposed into the introductory opening, through the entire housing including the lead terminal passageway and into a lead, with an interior electrically conductive portion electrically conductive with the exterior electrically conductive portion, the interior electrically conductive portion mechanically and electrically engageable with a multi-conductor lead terminal component to electrically engage a first conductor of the lead terminal component while the multi-conductor lead terminal component is located in the lead terminal passageway; and
   a securing contact device incorporated with the housing and accessible from outside the housing while a stylet is disposed into the introductory opening, through the entire housing including the lead terminal passageway and into a lead, the securing contact device configured to mechanically fix the multi-conductor lead terminal component to the housing to rotate the multi-conductor lead terminal component with the housing, the securing contact device further configured to electrically engage a second conductor of the multi-conductor lead terminal component through the housing to provide an electrical contact to the multi-conductor lead terminal component, the electrical contact spaced apart from the multi-conductor lead terminal component.

2. The apparatus as recited in claim 1, wherein the securing contact device is adapted to be in electrical communication with a lead terminal pin to provide a terminal adapted to electrically engage an analyzer conductor with the lead terminal pin.

3. The apparatus as recited in claim 1, wherein the exterior electrically conductive portion is electrically engageable with an analyzer conductor and the interior electrically conductive portion is electrically engageable with a lead terminal ring.

4. The apparatus as recited in claim 1, wherein the introductory opening includes a first diameter, the first diameter continuously narrowing to a diameter larger than an outer diameter of a stylet.

5. The apparatus as recited in claim 1, wherein the housing further includes one or more notch, the one or more notch is adapted to align with a position of a lead terminal pin when inserted into the lead terminal passageway.

6. The apparatus as recited in claim 1, wherein one or both of the at least one protective terminal contact device and the securing contact device include a terminal polarity contact indicator, each terminal polarity contact indicator providing a user-detectable electrical polarity indication of a lead component to which the at least one protective terminal contact device or the securing contact device is adapted to contact.

7. The apparatus as recited in claim 1, wherein one or both of the at least one protective terminal contact device and the securing contact device are radiopaque.

8. The apparatus as recited in claim 1, wherein the housing includes a housing first section and a housing second section, the housing second section is rotatable independent from the housing first section.

9. The apparatus as recited in claim 1, further comprising a rotational handle, a rotational handle first end of the rotational handle couplable to, and matable with, the housing.

10. The apparatus as recited in claim 1, wherein the lead terminal passageway is insertable over a lead terminal pin and at least a portion of one or more lead terminal rings with the electrically conductive portion of the at least one protective terminal contact device mechanically and electrically engageable with at least one lead terminal ring.

11. An apparatus comprising:
   a housing, including a lead terminal passageway insertable over a lead terminal pin and at least a portion of one or more lead terminal rings on a housing first end, and including an introductory opening on a housing second end, the lead terminal passageway and the introductory opening communicatively coupling within the housing;
   a securing contact device extending through the housing to provide an electrical contact to the lead terminal pin, the electrical contact spaced apart from the lead terminal pin, the securing contact device accessible from outside the housing while a stylet is disposed into the introductory opening, through the entire housing including the lead terminal passageway and into a lead, the securing contact device including a first position adapted to allow the lead terminal pin to be inserted within the housing and a second position adapted to mechanically engage the conductive lead terminal pin thereto with the lead in alignment with the housing to mechanically fix the lead to the housing to rotate the lead with the housing; and
   at least one protective terminal contact device, each protective terminal contact device including an exterior electrically conductive portion accessible from outside the housing while a stylet is disposed into the introductory opening, through the entire housing including the lead terminal passageway and into a lead, with an interior electrically conductive portion electrically conductive with the exterior electrically conductive portion, the interior electrically conductive portion mechanically and electrically engageable with a conductive lead terminal ring.

12. The apparatus as recited in claim 11, wherein one or both of the securing contact device and at least one protective terminal contact device include a terminal polarity contact indicator, each terminal polarity contact indicator providing a user-detectable electrical polarity indication of a lead component to which the securing contact device or the at least one protective terminal contact device is adapted to contact.

13. The apparatus as recited in claim 11, wherein the housing further includes a housing first section and a housing second section, the housing second section rotatable independent from the housing first section.

14. The apparatus as recited in claim 11, wherein the lead terminal passageway and the introductory opening communicatively couple within the housing defining a stylet receiving and withdrawing path.

15. The apparatus of claim 11, wherein a housing rotation handle is coupled to the housing.

16. The apparatus of claim 15, wherein a distal portion of the lead includes a helix shaped fixation portion.

17. An apparatus comprising:
   a multi-conductor lead extending from a lead terminal end to a lead distal end, the lead terminal end including a conductive lead terminal pin and at least one conductive lead terminal ring electrically insulated from the lead terminal pin;
   a housing, including a lead terminal passageway on a housing first end and an introductory opening on a housing second end, the lead terminal passageway insertable over at least a portion of the lead terminal end, the lead terminal passageway and the introductory opening communicatively coupling within the housing;
   at least one protective terminal contact device incorporated with the housing, each protective terminal contact device including an exterior electrically conductive portion accessible from outside the housing while a stylet is disposed into the introductory opening, through the entire housing including the lead terminal passageway and into a lead, with an interior electrically conductive portion electrically conductive with the exterior electrically conductive portion, the interior electrically conductive portion mechanically and electrically engageable with the at least one lead terminal ring; and
   a securing contact device incorporated with the housing and accessible from outside the housing while a stylet is disposed into the introductory opening, through the entire housing including the lead terminal passageway and into a lead, the securing contact device adapted to mechanically fix the lead terminal pin to the housing to rotate the lead terminal pin with the housing, the securing contact device further configured to electrically engage the lead terminal pin through the housing to provide an electrical contact to the lead terminal pin, the electrical contact spaced apart from the lead terminal pin.

18. The apparatus as recited in claim 17, further comprising a stylet insertable through the introductory opening.

19. The apparatus as recited in claim 17, further comprising a rotational handle, a first end of the rotational handle engageable with the housing.

\* \* \* \* \*